(12) United States Patent
Mikhail et al.

(10) Patent No.: US 9,936,884 B2
(45) Date of Patent: Apr. 10, 2018

(54) METHOD AND SYSTEM FOR TREATING HYPOTENSION

(76) Inventors: Megan Mikhail, Chapel Hill, NC (US); Charlotte Anne Guertler, Dover, MA (US)

( * ) Notice: Subject to any disclaimer, the term of this patent is extended or adjusted under 35 U.S.C. 154(b) by 1918 days.

(21) Appl. No.: 12/913,095

(22) Filed: Oct. 27, 2010

(65) Prior Publication Data
US 2011/0098580 A1 Apr. 28, 2011

Related U.S. Application Data

(60) Provisional application No. 61/255,741, filed on Oct. 28, 2009.

(51) Int. Cl.
| | | |
|---|---|---|
| *A61B 5/021* | (2006.01) | |
| *A61M 5/31* | (2006.01) | |
| *A61B 5/0215* | (2006.01) | |
| *A61M 5/142* | (2006.01) | |
| *A61M 5/145* | (2006.01) | |
| *A61B 5/00* | (2006.01) | |

(52) U.S. Cl.
CPC ............ *A61B 5/0215* (2013.01); *A61B 5/411* (2013.01); *A61B 5/4839* (2013.01); *A61B 5/6846* (2013.01); *A61M 5/1454* (2013.01); *A61M 5/14248* (2013.01); *A61B 5/0031* (2013.01); *A61B 2562/028* (2013.01); *A61M 2005/14252* (2013.01)

(58) Field of Classification Search
CPC ......... A61B 5/0215; A61B 5/021; A61B 5/01; A61B 5/0205; A61B 5/02055; A61B 5/0031; A61B 5/412; A61B 17/1325; A61B 2018/00404
See application file for complete search history.

(56) References Cited

U.S. PATENT DOCUMENTS 6,165,155 A * 12/2000 Jacobsen et al. ............. 604/156

OTHER PUBLICATIONS

Muraro et al. ("The management of anaphylaxis in childhood", Allergy 2007: 62: 857-871).*
Amer & Badawy ("An Integrated Platform for Bio-Analysis and Drug Delivery", Current Pharmaceutical Biotechnology, 2005, 6, 57-64).*
Focus Group for New Epinephrine Dispenser—hosted by BU Students (Sep. 28, 2009) teaches a wearable epinephrine dispenser.*
(Continued)

*Primary Examiner* — Patricia Mallari
*Assistant Examiner* — Michael J Burrage
(74) *Attorney, Agent, or Firm* — Murphy, Bilak & Homiller, PLLC

(57) ABSTRACT

A system and method for treating hypotension in a mammal including a measuring device for measuring the blood pressure in a blood vessel having a wireless transmitter therein for emitting a signal when the measured blood pressure moves into a predetermined range. The system also includes an injection device fixed on the skin of a mammal, the injection device having a receiver for receiving the signal emitted from the wireless transmitter, a drug reservoir, a conduit for moving drug from the drug reservoir through the skin upon activation, and an activation device that causes the drug to move from the drug reservoir through the conduit and into the mammal upon receiving the signal emitted from the wireless transmitter.

8 Claims, 4 Drawing Sheets

(56) References Cited

OTHER PUBLICATIONS

Cong et al. ("Novel Long-Term Implantable Blood Pressure Monitoring System with Reduced Baseline Drift"; Proceedings of the 28th IEEE EMBS Annual International Conference; Aug. 30-Sep. 3, 2006).*

Amer & Badawy ("An Integrated Platform for Bio-Analysis and Drug Delivery", Current Pharmaceutical Biotechnology, vol. 6, No. 1, pp. 57-64; Feb. 2005).*

Muraro et al. ("The management of anaphylaxis in childhood", Allergy, vol. 62, Iss.8, pp. 857-871; Aug. 2007).*

Chen et al. ("Improving blood-compatibility of titanium by coating collagen-heparin multilayers"; Applied Surface Science 255; Mar. 17, 2009).*

* cited by examiner

METHOD AND SYSTEM FOR TREATING HYPOTENSION

This application bases its priority on provisional application Ser. No. 61/255,741 filed Oct. 28, 2009 and which is incorporated herein in its entirety.

A method and system for treating hypotension in a mammal comprising a device for measuring the blood pressure in a blood vessel combined with an injection assembly administering a drug to the mammal.

DESCRIPTION

Each year, anaphylactic shock causes hundreds of deaths and over 30,000 visits to the emergency room in the United States alone. The most effective treatment for anaphylaxis is immediate injection of epinephrine, commonly known as adrenaline, into a muscle. Currently, manual injection devices are the only commercially available option. Severe allergy sufferers must constantly carry such devices to ensure adrenaline is immediately available in the case of an allergic reaction. This is dangerous, as well as inconvenient, since allergy sufferers are usually unable to inject themselves during anaphylactic shock.

A system that provides accurate and continuous. Detection of blood pressure combined with a wearable injection assembly would provide severe allergy sufferers with a reliable and convenient way of treating an anaphylactic episode. Such a system would prevent deaths by ensuring that people receive adrenaline during anaphylactic shock while allowing for greater freedom and peace of mind.

First Embodiment

Figure 1:
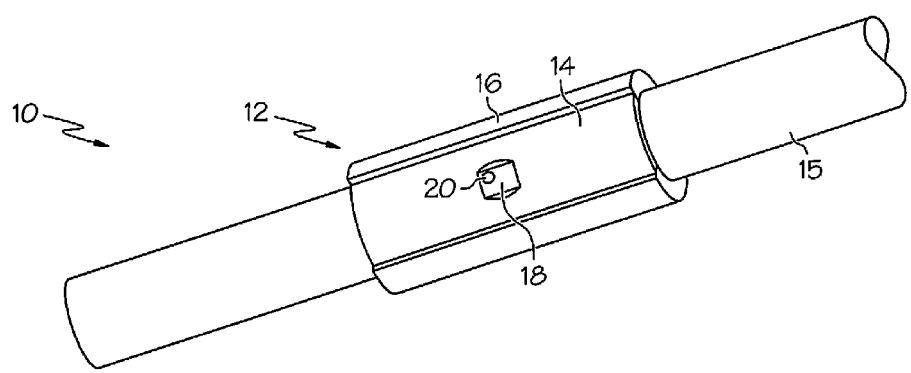
FIG. 1 is a perspective cut-away view of the first embodiment transmitter assembly shown in its installed position.

A first embodiment described herein is directed to a system for detecting a significant blood pressure drop, as a result of an anaphylactic shock or other malady, and treating such condition with an immediate injection of drug, such as adrenaline. The first embodiment 10 shown in FIG. 1 includes a microelectromechanical, or "MEMS" sensor 12.

MEMS devices are typically 1 to 1000 micrometers in length (a human hair is about 50 μm thick). Most MEMS devices are built through the layering of photosensitive materials with patterns created by light exposure. Silicon is commonly used for MEMS because of its reliability, low cost, and long history in integrated circuit technology. MEMS have a variety of applications, from accelerometers to blood pressure sensors.

The MEMS sensor 12 in the first embodiment wraps directly and completely around the artery, preferably the aortic artery, and can determine blood pressure through the expansion and contraction of the blood vessel. The MEMS sensor 12 includes a silicon pressure sensor band 14 that surrounds the aorta 15. The band 14 expands and contracts with the blood vessel, creating voltages in the sensor 12 that vary with blood pressure. When blood pressure drops, the artery diameter expands and thus provides an electronic indicator of blood pressure.

The first embodiment also includes a casing 16 to protect the MEMS sensor band 14. The casing is preferably made of heparin coated titanium and is designed to protect the MEMS sensor band 14 from any degradation or damage and reduce reactivity in the body.

The first embodiment further includes a wireless transmitter 18, such as a radio transmitter, incorporated into the MEMS device 12. The transmitter 18 is fixed to the MEMS sensor by thermal bonding and is powered by a medical grade pacemaker battery 20, such as lithium iodide, to provide the necessary power. When the sensor 12 generates a voltage below the calculated value for 70 mmHg, the transmitter 18 is programmed to emit a radio frequency.

Figure 2:
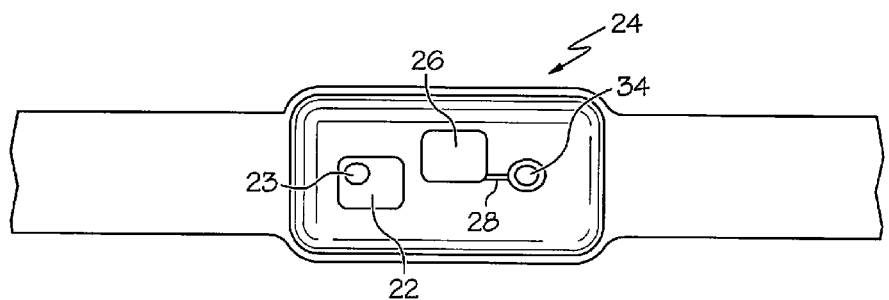
FIG. 2 is a top view of the first embodiment injection assembly.

The first embodiment 10 also includes a wireless receiver 22, such as a radio receiver, to receive the signal emitted from the transmitter 18 as shown in FIG. 2. The receiver 22 includes a receiver battery 23 to provide power to the receiver. The receiver battery 23 may also be lithium iodide. The receiver 22 is located within an injection assembly 24, along with a drug reservoir 26, conduit 28, and a spring loaded needle assembly 34. The injection assembly 24 may resemble a large rigid or semi-rigid bandage.

Figure 3:
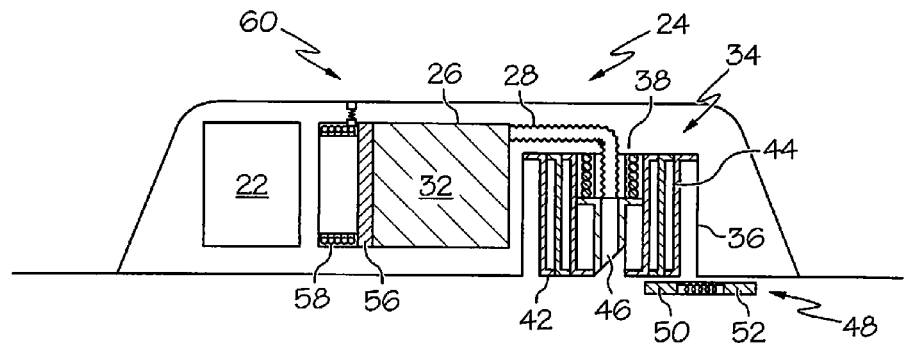
FIG. 3 is a side sectional view of the first embodiment injection assembly of FIG. 2.
Figure 3A:
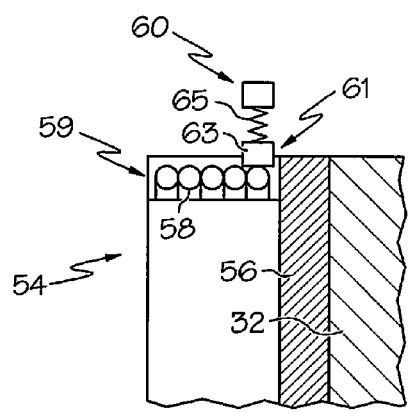
FIG. 3A is an enlarged portion of the drug reservoir activation mechanism of FIG. 3.
Figure 3B:
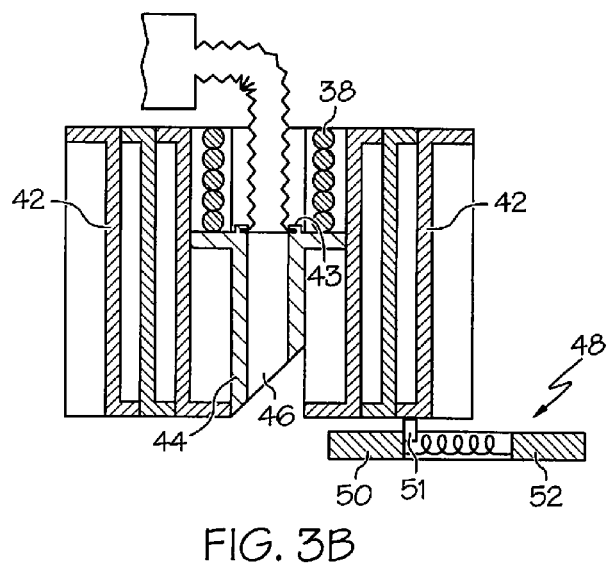
FIG. 3B is an enlarged view of the spring loaded needle assembly of FIG. 3.

The drug reservoir 26, as shown in FIG. 3, of the injection assembly 24 includes a rigid or semi-rigid housing 36. The housing 36 encloses the drug reservoir 26 which holds a fixed volume of liquid drug 32, such as adrenaline. The conduit 28 of the injection assembly 24, provides a pathway for the drug 32 into the spring loaded needle assembly 34. The spring loaded needle assembly 34 includes a coiled spring 38, a telescopically assembled injection needle 40. The telescopic needle 40 includes a plurality of lengths 42 and a sharpened needle end 44. The plurality of needle lengths 42 are received into other lengths of greater diameter during storage. The needle end 44 has a hollow portion 46 that connects to the conduit 28 via a hub 43. The conduit 28 must be sufficiently flexible and expandable to be stored in a retracted position and to expand to connect the drug 32 flowing from the reservoir 26 into the hub 43 upon activation. The injection assembly 24 of the first embodiment 10 also includes a needle activation mechanism 48, shown in FIG. 3B, for activating the injection assembly when the receiver 22 receives a signal that the blood pressure has dropped below a predetermined amount. The needle activation mechanism 48 includes a plate 50 that obstructs the spring 38 outward extension. The plate 50 is connected to a retractor mechanism 52 that retracts the plate, by spring or otherwise, from obstructing the natural extension of the spring 38 during activation. A holding pin 51 or other mechanism holds the plate 50 in place to prevent the nature expansion of the coiled spring 38 and thus the unwanted activation of the needle 40.

The drug reservoir also has a drug activation assembly 54 that includes a plunger 56, a plunger spring 58, and a drug reservoir activation mechanism 60, as seen in FIG. 3. The plunger spring 58 is housed within a sleeve 59 having a recess 61 therein. A holding plate 63 sits within the recess prior to activation. In use, the holding plate 63 is retracted by means of a retraction spring 65 or other mechanism. This frees up the travel of the plunger spring 58 which places pressure on the plunger 56. The plunger 56 is pushed along the length of the drug reservoir. 26 by the plunger spring 58 when the first embodiment 10 is activated. The plunger spring 58 forces the plunger 56 along the length of the drug reservoir 26 thus causing the volume of drug 32 therein to move out of the drug reservoir, through the conduit 28, and through the hollow portion of the needle 46 and into the tissue of the user.

In use, the MEMS device 12 of the first embodiment 10 is fixed to a location along the exterior circumference of the aortic artery of the user. This is accomplished by an invasive procedure. It should be noted that while the aortic artery is the preferred location for the MEMS device 12, other arteries and veins may be used. The injection assembly 24 is fixed to a location along the skin surface of the user, preferably the thigh. The injection assembly 24 may be fixed to the user by means of a belt or strap, or elasticized cuff, or it may be fixed by means of an adhesive, such as that used on bandages.

Figure 6:
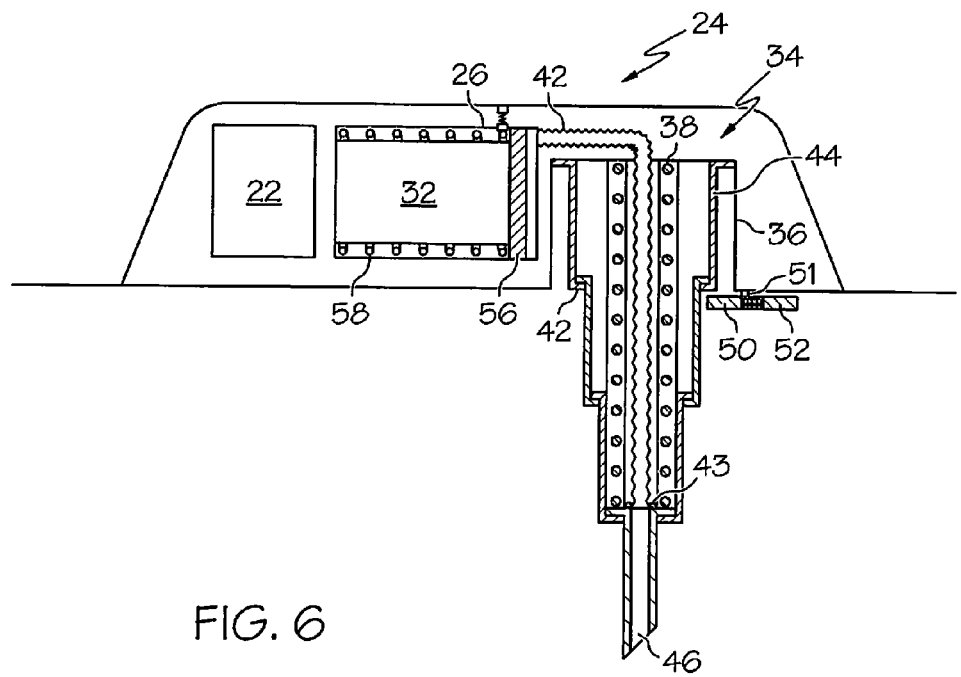
FIG. 6 is a side sectional view of the first embodiment injection assembly in its activated position.
Figure 7:
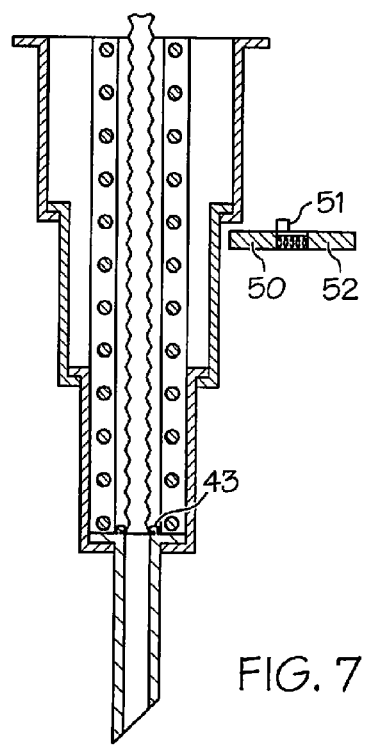
FIG. 7 is a close up of the injection needle assembly of the embodiment of FIG. 6.

When the user's blood pressure drops below 70 mmHg systolic (normal is 120 mmHg), the MEMS device 12 senses the change as a voltage change and the transmitter 18 emits a radio frequency. The receiver 22 in the injection assembly 24 receives the emitted frequency. This frequency activates the activation mechanism 52. The activation mechanism 52 causes the holding pin 51 to retract so that the plate 50 may move from obstructing the natural extension of the spring 38. As a result, the spring 38 extends pushing the telescopic needle 40 and all of its lengths 44 downward so that the needle tip moves into the user's tissue, as shown in FIGS. 6 and 7. Concurrently, the receiver 22 activates the drug reservoir activation mechanism 60 which releases the holding plate 63 from the recess 61 thus enabling the natural travel of the plunger spring 58. This causes the drug 32 in the drug reservoir 26 to move from the drug reservoir through the conduit 28 and the hollow portion 46 of the needle assembly 34, through the skin and into the tissue of the user, as shown in FIG. 6.

It is preferable that the needle length and position, upon activation, are capable of delivering the drug intramuscularly. It is further anticipated that the injection assembly and in particular, the drug reservoir volume, be adjustable to provide for various dose levels for a variety of users. For example in treating hypotension induced by anaphylaxis, the drug reservoir may contain either 0.3 mg or 0.15 mg of adrenaline, depending on weight of the user.

A Second Embodiment

Figure 4:
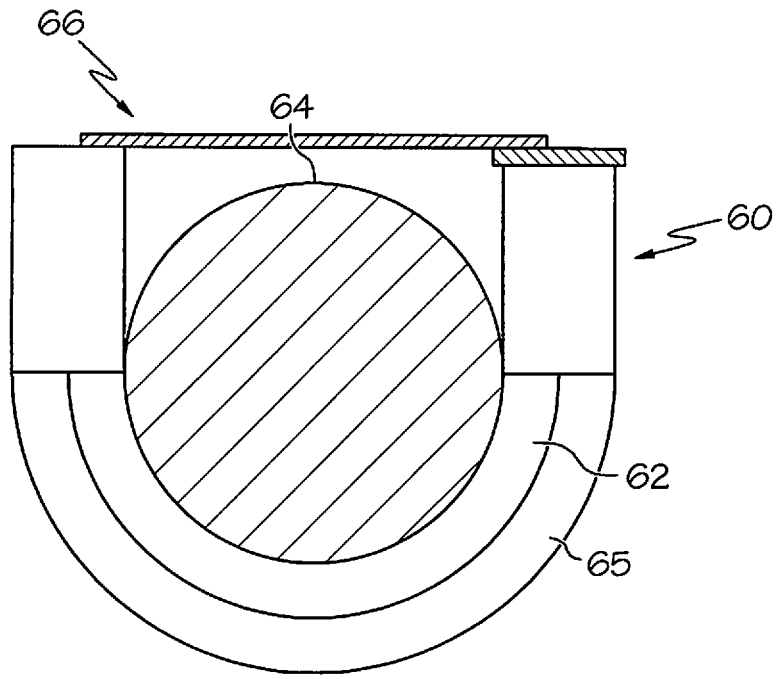
FIG. 4 is a side sectional view of the second embodiment transmitter assembly shown in its installed position.
Figure 5:
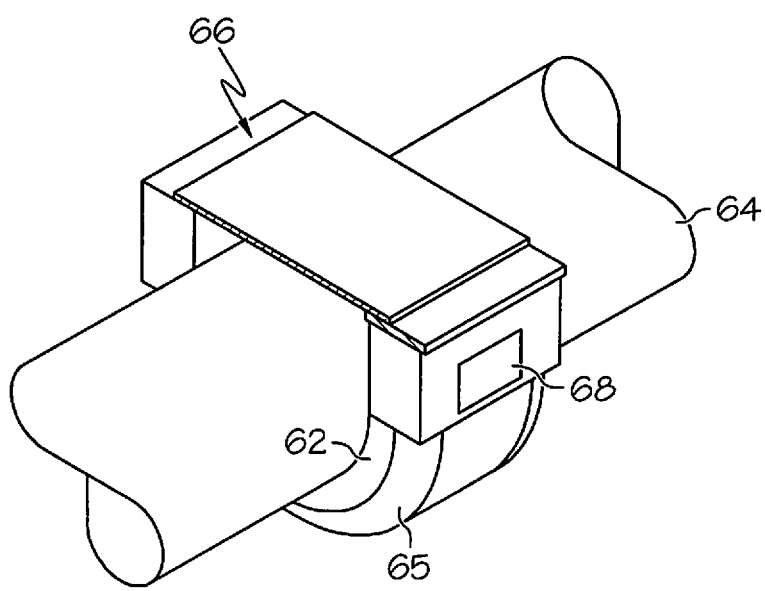
FIG. 5 is a perspective view of the transmitter assembly of FIG. 4.

A second embodiment 60 is directed to a system and method for the measurement and treatment of low blood pressure as a result of an anaphylactic shock episode or the like. The second embodiment system includes a MEMS device 62, shown in FIGS. 4 and 5, surrounding a portion of the exterior circumference of an artery 64. The MEMS device 62 is made of similar material as described above and functions in the same way as described above. The MEMS device 62 expands and contracts with the change in blood pressure of the artery 64. It is preferred that the artery is the aortic artery. A protective sleeve 65 surrounds the MEMS device 62 to protect it from damage as discussed above with regard to the casing 16 in the first embodiment 10. A silicon plate 66 is linked to the MEMS device 62 so that the entire circumference of the artery 64 is surrounded by either the MEMS device or the silicon plate. The silicon plate 66 acts like a switch with the MEMS device 62, moving out of contact with the MEMS device when the artery expands radially beyond a predetermined measurement. A radio transmitter 68, incorporated within the MEMS device, 62 emits a signal when the silicon plate 66 is in contact with the MEMS device. The lack of contact between the MEMS device 62 and the silicon plate 66 interrupts the signal being emitted from transmitter 68. The second embodiment 60 further includes a radio receiver 22 similar to one identified with regard to the first embodiment 10, to receive the transmission from the radio transmitter 68. The receiver 22, and injection assembly 24 are similar in structure and function as the first embodiment 10. Thus reference will be to the same items and numerals as described above. The second embodiment 60 directed to treating hypotension also includes the same injection assembly 24 fixed on the skin of a mammal. When the signal emitted from the radio transmitter 68 is interrupted as a result of disengagement of the silicon plate 66 from the MEMS device 62, the receiver 22 activates the drug reservoir-activation mechanism 48 and the needle activation mechanism to move drug 32 out of the reservoir 26 through the conduit 28, through the hollow portion 46 of the needle assembly 34 and into the tissue of the user, as described in more detail above. In order to determine how far above the blood vessel the silicon plate 66 needed to be located in order to disrupt the circuit at blood pressures below 70 mmHg, the expansion of blood vessels as a function of pressure using Poiseuille's equation was calculated for laminar flow of viscous fluids through a cylindrical pipe:

$$Q = \frac{\pi (\Delta P)(r)^4}{8(\eta)(L)}$$

Equation 1 where Q is the volumetric flow rate, $\Delta P$ is change in pressure across the vessel, r is radius, $\eta$ is viscosity, and L is length. The volumetric flow rate, Q, for a 1 cm long brachial artery with a 1.9 mm radius at 120 mmHg and standard blood viscosity of 0.0027 Pa*s was calculated to be 0.0030 m2/s.

Using the definition of volumetric flow rate:

$Q = a(v)$ $a_1 v_1 = a_2 v_2$ $Q_1 = Q_2$

Equation 2

The radius of the same brachial artery was calculated at a pressure of 70 mmHg to be 2.2 mm, a 0.3 mm increase. Therefore, it was determined that it is possible to disrupt the circuit and trigger activation of the injection assembly 24 when blood pressure drops below 70 mmHg by placing the silicon plate 0.3 mm above the artery.

In use, as discussed above, the MEMS device 62 and silicon plate 66 are implanted in the same fashion described above so that the device and plate completely surround the artery 64. When the patient's blood pressure drops below a predetermined amount (preferably 70 mmHg), the silicon plate 66 is deflected radially outward as a result of the expansion of the artery 64 diameter. This deflection causes an interruption in the signal emitted by the transmitter 68. The receiver 70 is programmed to react to the interruption of the signal and activates the injection assembly 24 as described previously to deliver drug 32 from the drug reservoir 26 into the user's tissue. As stated above, it is preferable that the drug be delivered intramuscularly.

It is anticipated that there may be other drugs used in the treatment of hypotension other than epinephrine or adrenaline, these include but are not limited to dopamine, dobutamine, and norepinephrine. It is further anticipated that other automatic injection technology other than that described herein may be user to deliver drug from a drug reservoir into the user in a timely fashion. For example, the needle activation mechanism 48 and drug reservoir activation assembly 54 could be activated by means other than springs. Hinges or a multitude of other devices could be used to activate these assemblies.

The invention claimed is:

1. A system for treating hypotension in a mammal comprising:
    a MEMS-based sensor configured to at least partly surround an artery of the mammal and to detect a drop in blood pressure of the mammal based on detecting a radial expansion of the artery, said MEMS-based sensor further configured to provide an indication of low blood pressure via a battery-powered wireless transmitter included in the MEMS-based sensor; and
    an injection device configured to be fixed on the skin of a mammal, the injection device having
        a wireless receiver configured to detect the indication of low blood pressure, as provided by the MEMS-based sensor via the wireless transmitter,
        a drug reservoir,
        a conduit for moving a drug from the drug reservoir through the skin upon activation, and
        an activation device that causes the drug to move from the drug reservoir through the conduit and into the mammal, responsive to the detected indication of low blood pressure;
    wherein the MEMS-based sensor includes a silicon pressure band having a displaceable segment comprising a silicon plate that is operative as a normally-closed switch, said silicon pressure band configured to surround the artery and dimensioned so that radial expansion of the artery beyond a predefined amount opens the switch, and further wherein the MEMS-based sensor is configured to provide the indication of low blood pressure responsive to the switch opening.

2. The system of claim 1 wherein the MEMS-based sensor is configured to provide the indication of low blood pressure responsive to detecting that the blood pressure has dropped to 70 mmHg or less.

3. The system of claim 1 wherein the drug is adrenaline.

4. The system of claim 1 wherein the conduit includes a needle.

5. The system of claim 1 wherein the injection device is configured to inject the drug into the muscle tissue of the mammal.

6. The system of claim 1 wherein the hypotension is a result of anaphylaxis.

7. The system of claim 1, wherein the MEMS-based sensor includes a heparin-coated titanium casing, to reduce a reactivity of the MEMS-based sensor in the body of the mammal after the MEMS-based sensor is invasively attached to the artery of the mammal.

8. The system of claim 1, wherein the silicon pressure band is dimensioned so that the switch opens when the blood pressure drops to 70 mmHg or less.

\* \* \* \* \*